US008082920B2

(12) United States Patent
Hughes

(10) Patent No.: US 8,082,920 B2
(45) Date of Patent: *Dec. 27, 2011

(54) ACOUSTIC RESPIRATORY THERAPY APPARATUS

(75) Inventor: Arthur R. Hughes, Parker, CO (US)

(73) Assignee: Vibralung, Inc., Parker, CO (US)

( * ) Notice: Subject to any disclaimer, the term of this patent is extended or adjusted under 35 U.S.C. 154(b) by 64 days.

This patent is subject to a terminal disclaimer.

(21) Appl. No.: 12/576,511

(22) Filed: Oct. 9, 2009

(65) Prior Publication Data

US 2010/0022923 A1 Jan. 28, 2010

Related U.S. Application Data

(62) Division of application No. 11/286,489, filed on Nov. 23, 2005, now Pat. No. 7,617,821.

(51) Int. Cl.
*A61M 15/00* (2006.01)
*A61M 16/00* (2006.01)
*A62B 7/00* (2006.01)
*A62B 9/00* (2006.01)
*A62B 18/00* (2006.01)

(52) U.S. Cl. .................. 128/200.24; 601/41; 482/13

(58) Field of Classification Search ............ 128/200.24, 128/202.28, 202.29; 601/41, 43, 46, 47, 601/107, 150; 482/13

See application file for complete search history.

(56) References Cited

U.S. PATENT DOCUMENTS

| 2,918,917 | A | 12/1959 | Emerson |
| 3,037,497 | A | 6/1962 | Roberson |
| 3,158,152 | A | 11/1964 | Bloom |
| 3,628,280 | A | 12/1971 | Nave |
| 3,863,914 | A | 2/1975 | O'Connor |
| 4,054,134 | A | 10/1977 | Kritzer |
| 4,062,358 | A | 12/1977 | Kritzer |
| 4,221,381 | A | 9/1980 | Ericson |
| 4,275,722 | A | 6/1981 | Sorensen |
| 4,297,999 | A | 11/1981 | Kitrell |
| 4,349,015 | A | 9/1982 | Alferness |
| 4,813,403 | A | 3/1989 | Endo |
| 5,018,517 | A | 5/1991 | Liardet |

(Continued)

OTHER PUBLICATIONS

International Search Report and Written Opinion from related International Application No. PCT/US2006/043777, mailed Aug. 16, 2007.

*Primary Examiner* — Justine Yu
*Assistant Examiner* — Colin W Stuart
(74) *Attorney, Agent, or Firm* — Greenberg Traurig, LLP

(57) ABSTRACT

An active respiratory therapeutic device for clearing breathing passages, loosening and breaking up mucus plugs and phlegm in a patient's sinuses, trachea, bronchial passages and lungs while a patient is breathing normally through the device is disclosed. The apparatus preferably includes a C shaped curved hollow housing having a closed end portion and an open threaded end portion. The open end portion forms at least part of an acoustic coupling chamber. A generally funnel shaped tapered mouthpiece tapers to a small end portion sized to be inserted into a patient's mouth. The mouthpiece forms another part of the acoustic coupling chamber. An acoustic signal generator housed within the hollow housing generates and directs acoustic vibrations into and through the coupling chamber. The mouthpiece preferably includes a valve permitting a patient breathing through the mouthpiece to inhale through a valve opening and exhale through a bypass passage around the valve while at the same time coupling the acoustic coupling chamber into the patient's airways.

8 Claims, 9 Drawing Sheets

U.S. PATENT DOCUMENTS

| | | |
|---|---|---|
| 5,193,529 A | 3/1993 | Labaere |
| 5,368,015 A | 11/1994 | Wilk |
| 5,451,190 A | 9/1995 | Liardet |
| 5,569,122 A | 10/1996 | Cegla |
| 5,628,305 A | 5/1997 | Melker |
| 5,647,345 A | 7/1997 | Saul |
| 5,829,429 A | 11/1998 | Hughes |
| 5,893,361 A | 4/1999 | Hughes |
| 6,058,932 A | 5/2000 | Hughes |
| 6,119,684 A | 9/2000 | Nohl et al. |
| 6,152,130 A | 11/2000 | Abrams et al. |
| 6,167,881 B1 | 1/2001 | Hughes |
| 6,190,337 B1 * | 2/2001 | Nedwell ............ 601/46 |
| 6,702,769 B1 | 3/2004 | Fowler-Hawkins |
| 6,848,443 B2 | 2/2005 | Schmidt et al. |
| 6,974,425 B2 * | 12/2005 | Rogers et al. ............ 601/46 |
| 7,232,417 B2 | 6/2007 | Plante |
| 7,617,821 B2 * | 11/2009 | Hughes ............ 128/200.24 |
| 2002/0077369 A1 | 6/2002 | Noolandi et al. |
| 2003/0226562 A1 * | 12/2003 | Schmidt et al. ......... 128/200.24 |
| 2004/0097850 A1 * | 5/2004 | Plante ............ 601/41 |

* cited by examiner

ACOUSTIC RESPIRATORY THERAPY APPARATUS

CROSS-REFERENCE TO RELATED APPLICATION

This Application is a divisional of U.S. patent application Ser. No. 11/286,489, filed on Nov. 23, 2005, which is incorporated herein by reference in its entirety.

BACKGROUND

1. Field

This disclosure generally relates to respiratory devices and more particularly to a vibrating device and method that assist in breaking up and dislodging accumulated fluids and solids generated or residing in a patient's lungs, respiratory tract or sinuses, and/or assist in opening constricted airway passages and sinus passages.

2. General Background

People and other animal patients that have lung diseases such as, among other things, cystic fibrosis, bronchiactasis, acute and chronic asthma, pneumonia, sinusitis, and chronic bronchitis, have a difficult time breaking up, dislodging, and expelling mucus, phlegm and other secretions and infectious materials that develop and/or reside in the lungs, sinuses and respiratory track. The presence of this material in the lungs, bronchial and tracheal passages, and sinuses, provides an excellent media for growth of bacteria. For treatment of the condition, rotation of antibiotics is often used to treat the bacterial infections that result. Postural drainage with induced vibration, percussive therapy and/or the use of a mechanical device such as a flutter valve are often used to help the patient dislodge this mucus material. Likewise, people and animals with constrictive airway diseases such as asthma and sinusitis have difficulty opening airway and sinus passages.

Several active acoustic respiratory therapy devices are described in my U.S. Pat. Nos. 6,058,932, 6167,881, 5,893,361, and 5,829,429. Each of these devices develops a series of acoustic vibrations, e.g. audible tones at various magnitudes and frequencies, which are directed through a patient's mouth and airways directly into the lungs, rather than through the damped tissue of the patient's chest wall as has heretofore been a standard percussive therapeutic practice.

SUMMARY

An acoustic respiratory therapy device in accordance with the present disclosure includes a number of novel improvements. One embodiment includes an elongated curved hollow housing having a closed end portion that may be optionally vented to atmosphere and an open end portion, the open end portion forming at least one part of an acoustic coupling chamber, a mouthpiece having one end adapted to fit onto the open end portion of the housing, and another end shaped to provide for delivery of acoustic energy generated by the device to the particular patient, whether the patient be human or other animal. In other embodiments, the closed end portion may be vented to the atmosphere, and the mouthpiece may have one end adapted to fit on the open end portion of the housing and the other end designed on any number of rigid or flexible shapes to provide for delivery of acoustic energy generated by the device to the patient.

The particular shape of the other end portion of the mouthpiece is preferably determined by the anatomy of the particular patient involved, whether human or other animal. For example, for humans, the other end may taper to an oval end that the patient can comfortably hold in his or her mouth. Alternatively, for example, in the case of large domestic animals, the other end of the mouthpiece may be shaped to fit into a patient's nasal passage or other delivery site.

The mouthpiece forms another part of the acoustic coupling chamber. In some embodiments the mouthpiece may include a valve operable to permit a patient breathing through the mouthpiece to inhale through a valve opening and exhale through a bypass passage around the valve while coupling the acoustic coupling chamber into the patient's mouth, nasal passage, or other delivery site. In other embodiments, however, the valve may be unnecessary.

An acoustic signal generator is housed within the hollow housing that has an acoustic transducer directing acoustic energy into and through the coupling chamber into a patient's airways when the mouthpiece is coupled into the patient's airways.

The valve in the device preferably is removable and has an elongated housing body having one or more passages extending from an open end of the housing to an exit aperture and a valve opening spaced from the exit aperture. A flexible valve disc is disposed in the valve opening that is operable to permit passage of a gas such as air through the valve opening in a first direction and block passage of the gas through the valve opening in a second direction. The valve allows passage of the gas in the second direction through restrictive openings to generate a back pressure during exhalation.

Stated another way, an exemplary embodiment is an apparatus for assisting a patient in opening constricted airway passages and/or in loosening phlegm, mucus and other secretions and potentially infectious materials collected in a patient's nasal passages, lungs, bronchial and/or tracheal passages that has an elongated curved hollow housing having a closed end portion and an open threaded end portion, the open end portion forming at least part of an acoustic coupling chamber. The closed end portion may optionally be open to atmosphere.

A generally funnel shaped tapered mouthpiece having a large end is adapted to fit onto the open end portion of the housing. The mouthpiece tapers to a smaller end portion sized to be inserted into a patient's mouth. The mouthpiece forms another part of the acoustic coupling chamber. The housing encloses a programmable acoustic signal generator preferably housed within a web portion of the housing between the closed end portion and the open end portion. The hollow housing has an acoustic transducer in the open end portion directing acoustic energy, typically in the form of acoustic vibrations, e.g. pressure pulses, into and through the coupling chamber into the patient's airways when the mouthpiece is held in the patient's mouth, nose, or other delivery site. The acoustic signal generator may include a microprocessor on a printed circuit board mounted in the web portion of the housing.

In a preferred embodiment, the web portion of the housing has a plurality of apertures therethrough aligned with contact pads on the internal printed circuit board for connecting a programmable computer to the apparatus, e.g., the microprocessor in the signal generator so that the generator may be programmed with predetermined acoustic profiles for optimal operation of the apparatus for a particular patient.

An embodiment of the apparatus preferably has a removable valve in the mouthpiece that has an elongated valve housing body having one or more passages extending from an open end of the valve housing to an exit aperture and a valve opening spaced from the exit aperture. A flexible valve disc is disposed in the valve opening which is operable to permit passage of a gas such as air through the valve opening in a first direction and block passage of the gas through the valve opening in a second direction. The valve allows passage of the gas in the second direction through restrictive openings to generate a back pressure during exhalation.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
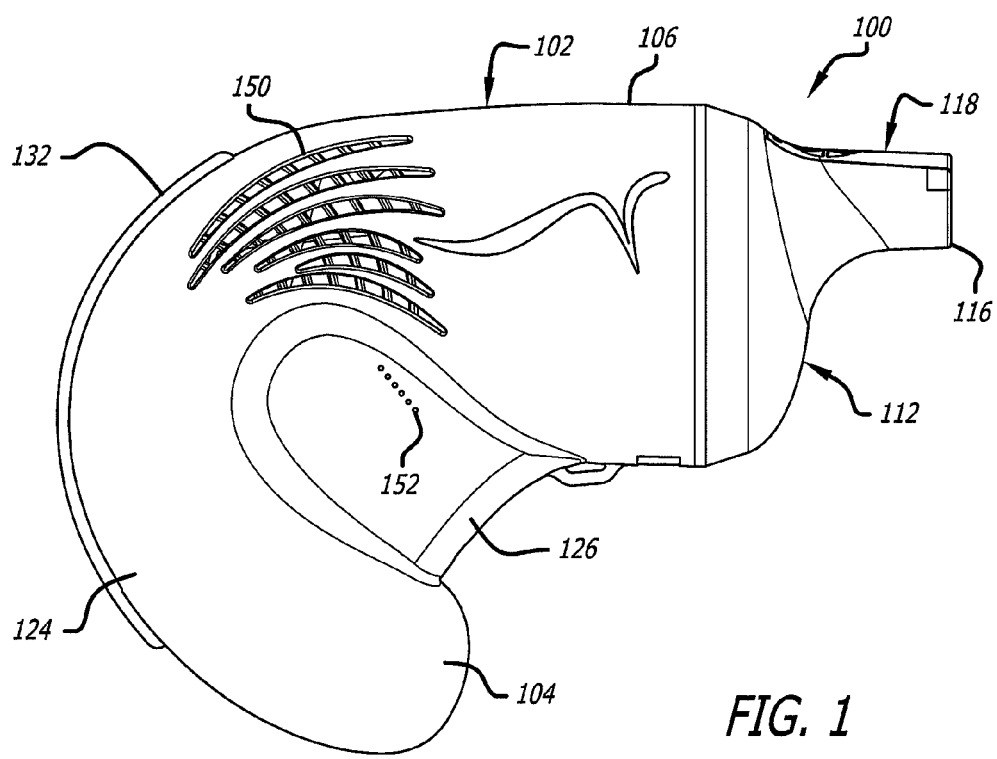
FIG. 1 is a right side view of one embodiment of the apparatus in accordance with the present disclosure.
Figure 2:
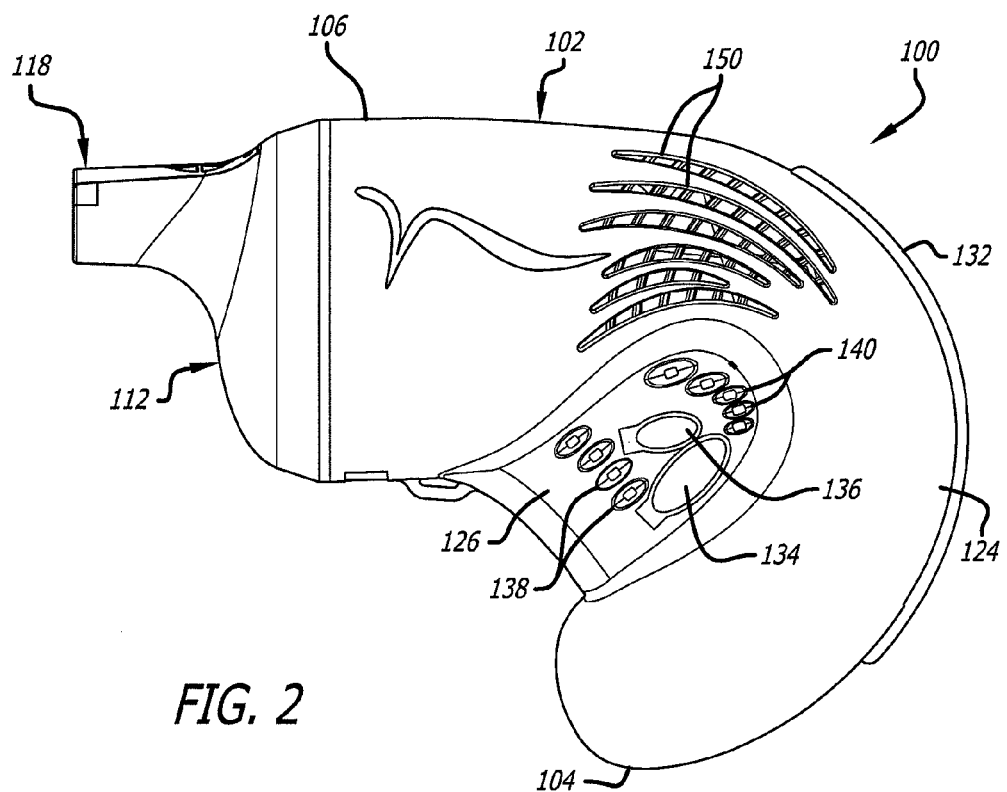
FIG. 2 is a left side view of the embodiment of the apparatus in accordance with the present disclosure shown in FIG. 1.
Figure 3:
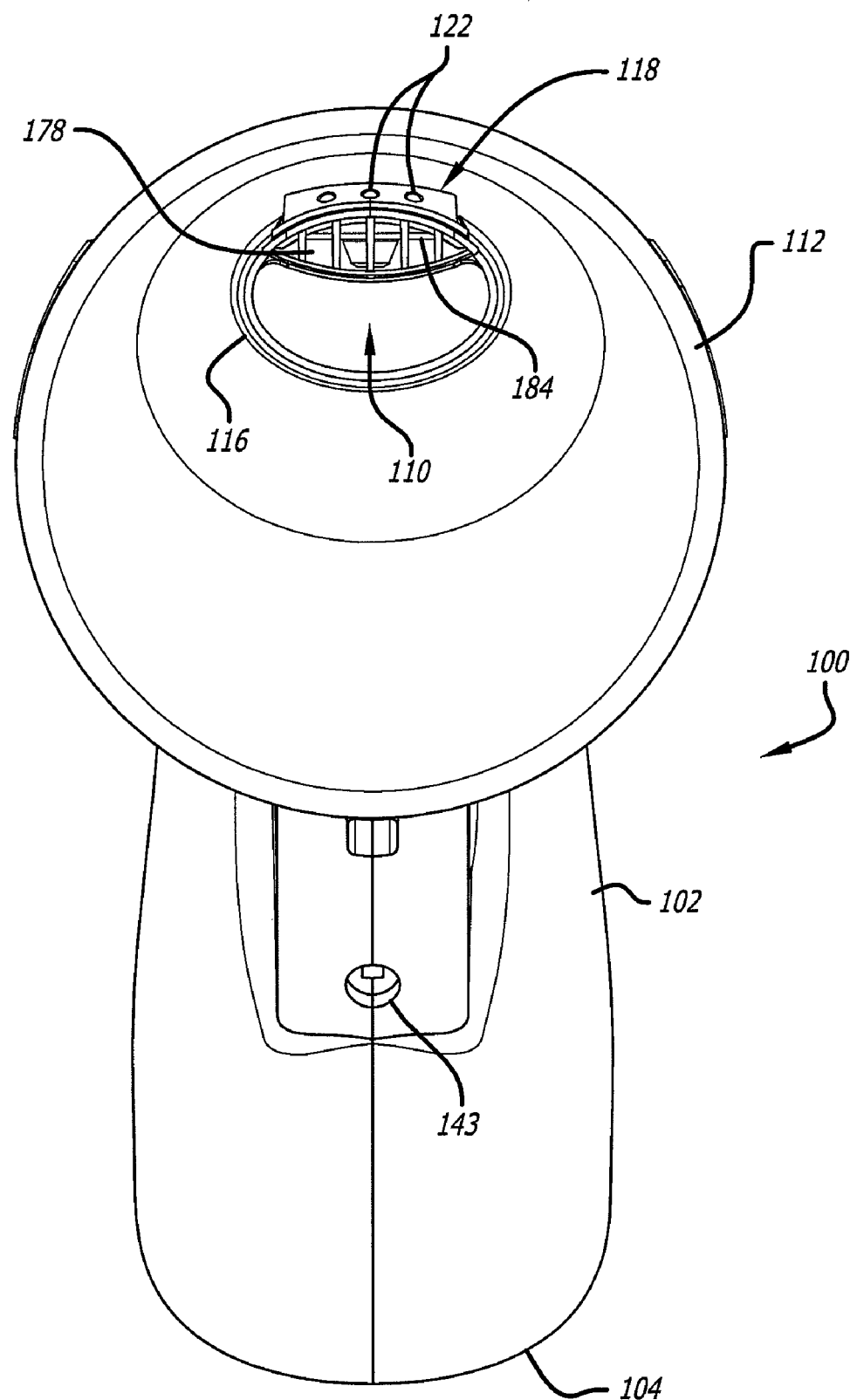
FIG. 3 is a patient's end view of the embodiment of the apparatus in accordance with the present disclosure shown in FIGS. 1 and 2.
Figure 6:
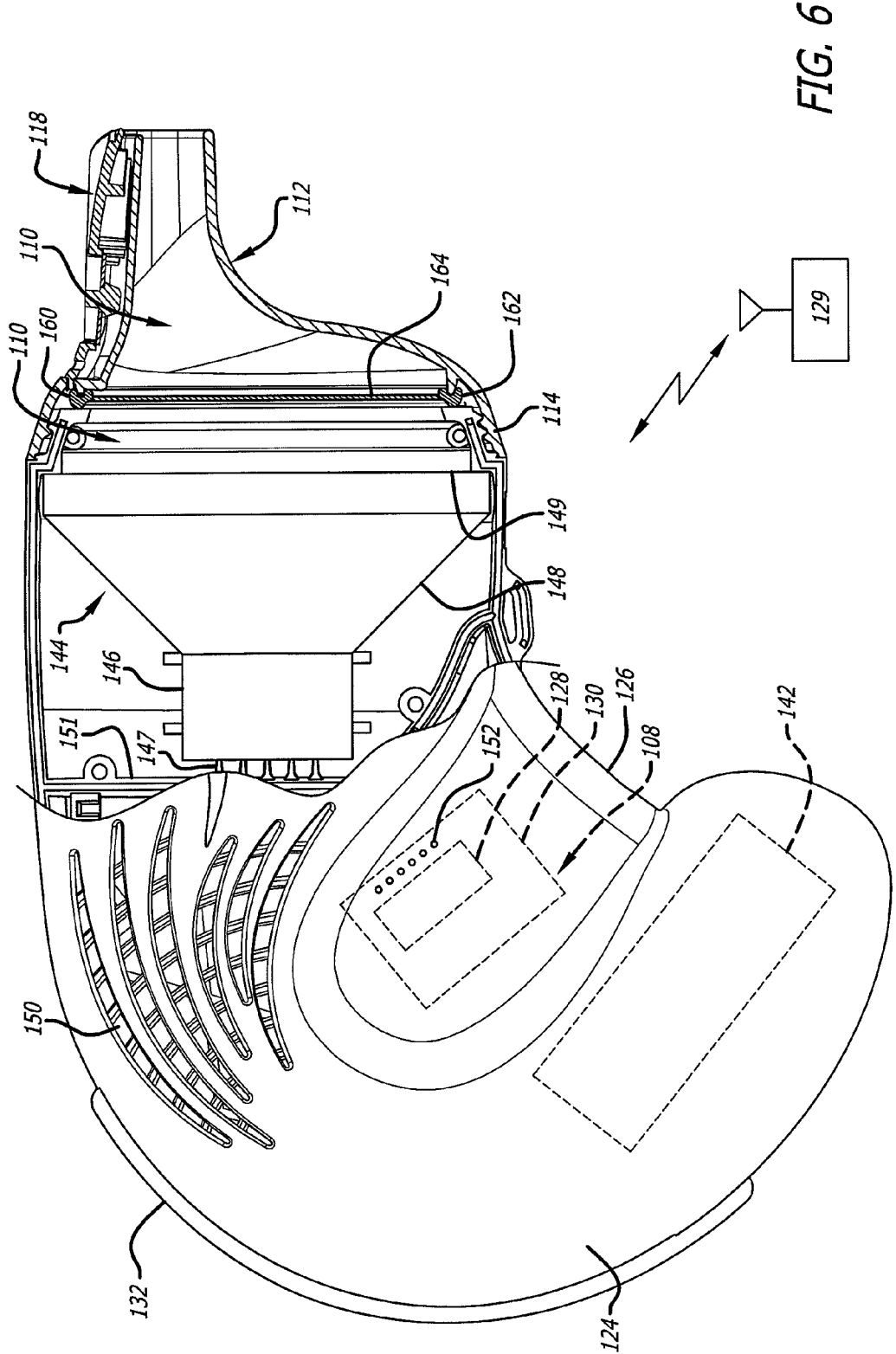
FIG. 6 is a side view as in FIG. 1 with portions broken away showing the internal structures of the acoustic chamber and mouthpiece in section.

One embodiment of an acoustic respiratory therapy apparatus 100 is shown in side views in FIGS. 1, 2, and 6 and in a patient end view in FIG. 3. The apparatus 100 has an elongated curved hollow housing 102 having a substantially closed end portion 104 and an open end portion 106. This open end portion 106 is preferably threaded. The housing 102 encloses an acoustic generator 108 and the open end portion 106 forms part of an acoustic coupling chamber 110.

A generally funnel shaped tapered mouthpiece 112 forms the other part of the acoustic coupling chamber 110. The mouthpiece 112 preferably has a large threaded end 114 that is adapted to fit onto the open threaded end portion 106 of the housing 102. The mouthpiece 112 preferably tapers to a smaller end portion 116 sized to be comfortably inserted into and held in a patient's mouth. For other animal patients, the mouthpiece may have a different shape consistent with the particular patient's physiology. The mouthpiece 112 preferably includes a valve 118 operable to permit a patient breathing through the mouthpiece 112 to inhale through a valve opening 120 and exhale through one or more bypass passages 122 around the valve 118 while coupling the acoustic coupling chamber 110 through the patient's mouth into the patient's airways.

This mouthpiece 112 may have a different shape than as shown in FIGS. 1-8 for different applications. For example, for use with animals or infants, the mouthpiece 112 may be shaped to cover both the patient's nose and mouth, or only through the patient's nose. As used in this specification, a patient's airways includes all of the passages into and out of the patient's lungs including the mouth, nose, trachea, bronchial tubes and the lung alveoli. The mouthpiece 112 shown in FIGS. 1-6 and 8 is preferably formed of a generally rigid plastic material such as a polypropylene copolymer but may alternatively be formed of other materials to suit the application. For example, the end portion 116 may be formed of a softer material joined to the large end 114.

Figure 8:
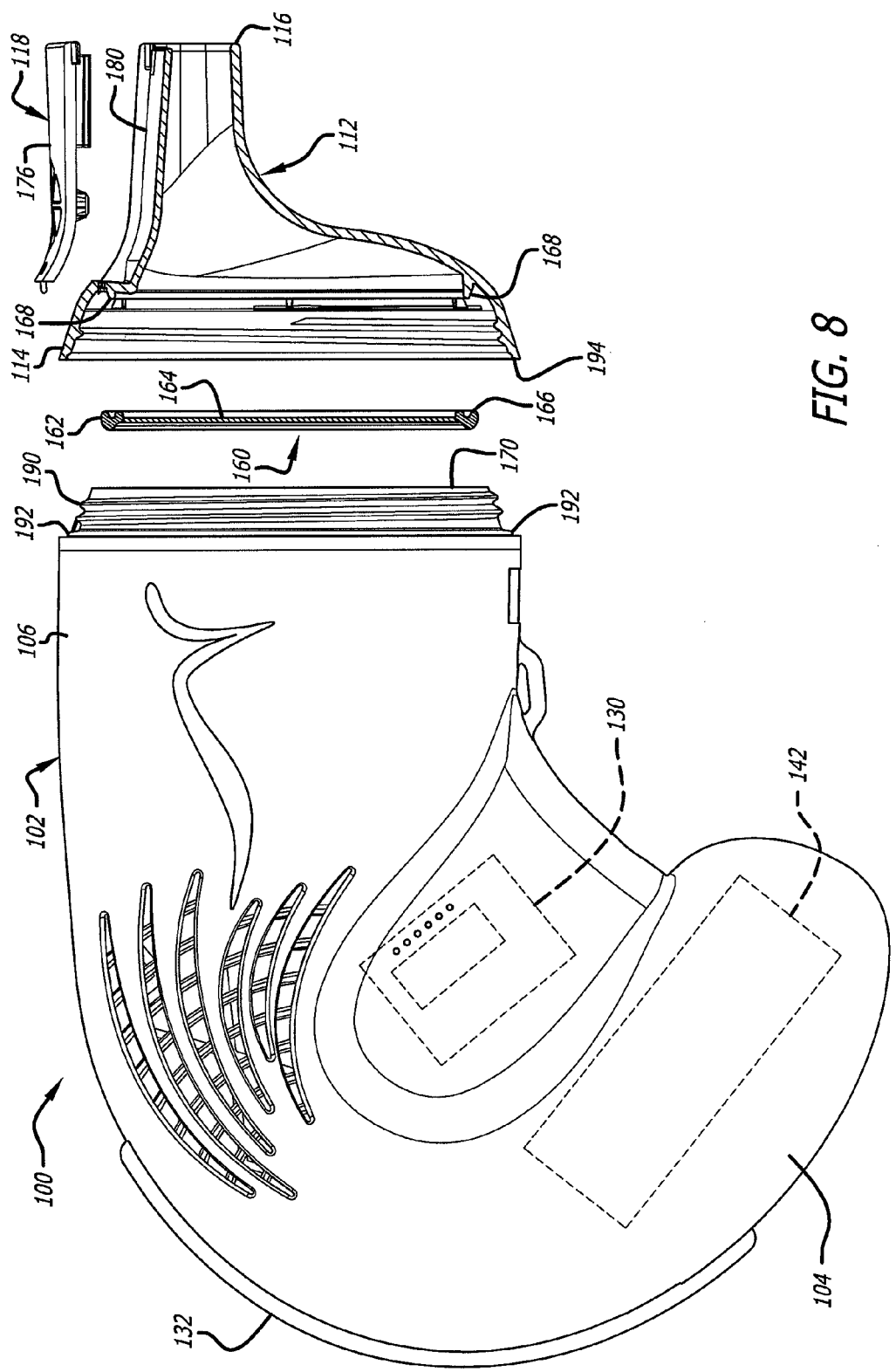
FIG. 8 is an exploded side view of the embodiment shown in FIG. 1.

The joint between the mouthpiece 112 and the housing 102 is shown in the drawings as preferably a threaded connection as shown in FIGS. 6 and 8. The threaded connection may involve internal threads on the housing open end 106 and mating external threads on the mouthpiece 112. Other suitable connections may alternatively be utilized. For example, an interlocking bayonet type arrangement such as is often utilized in cameras to join a lens to a camera body could be used.

In the embodiment 100 shown in the Figures, the housing 102 is an injection molded "C" shaped curved hollow plastic body having a curved back 124 between the closed end portion 104 and the open end portion 106. The housing 102 is preferably made of an injection molded plastic material, but may alternatively be formed of other materials and using other processes. The closed end portion 104 may alternatively vent to atmosphere so as to dissipate heat generated during charging and discharging of a battery 142. The housing 102 preferably has a hollow web portion 126 spanning between the end portions 104 and 106. This web portion 126 preferably houses portions of the acoustic generator 108, specifically a microprocessor 128 mounted on a control circuit board 130 therein for selectively controlling the volume, frequency, pulse and repetition rate of the acoustic vibrations generated by the acoustic generator 108.

An elongated slide switch 132 is mounted to the curved back 124 of the housing 102. This slide switch 132 can be moved up and down along the curved back 124 and may be used to change the pitch or frequency of the acoustic vibrations generated. The slide switch may be used to control other device functions or have no control function at all, depending on the intended patient use. Other placements and configurations of the slide switch 132 are alternatively envisioned. Placement of the switch 132 along the curved back 124 has been found during testing to be a comfortable and convenient location for a human patient.

The web portion 126, as is shown in FIG. 2, has a pair of operational control buttons 134 and 136, and a series of indicators 138 and 140. The control button 134 is used to turn power to the control circuits of apparatus 100 on and off. Control button 136 is multi-functional. It is to be understood that the particular functions of the individual control buttons 134 and 136 are merely exemplary and thus the particular function assigned may be different than as described herein. In the particular embodiment of the apparatus 100 shown in FIGS. 1-8, the button 136 preferably is used to select a desired mode of operation, select a frequency mode, select a desired repetition rate and select desired volume. This button 136 may be further defined to provide for additional functional modes programmed into the microprocessor 128 described below. The relative volume, relative frequency, and battery charge level are selectively indicated by the series of indicators 140. The mode of operation is indicated by the series of indicators 138. As previously mentioned, analog adjustment of frequency is preferably controlled by the slide switch 132. However, any of the control buttons and/or side switch may alternatively be provided with such functionality.

The acoustic generator 108 comprises a power supply, a programmable microprocessor 128, audio amplifier circuitry and controls on the circuit board 130, and an acoustic transducer 144. The power supply is preferably a rechargeable battery 142 such as a metal nickel hydride or lithium ion battery pack that can be recharged through an appropriate charger connector 143 (FIG. 3). Although not shown, the section 104 may have spaced openings or vents to provide some air circulation cooling during battery pack recharging as well as heat dissipation during use of the apparatus 100.

In the embodiment 100 illustrated, the transducer 144 is an audio speaker. This transducer 144 has a magnet 146 around a moving voice coil (not shown) coupled to a flexible audio cone 148. Movement of the voice coil back and forth produces the acoustic vibrations in front of the cone 148 that are directed through the coupling chamber 110 into a patient's airways. The audio cone 148 thus forms part of the boundary of the coupling chamber 110. A plurality of ventilation slit openings 150 in the housing 102 behind the transducer 144 facilitates convective removal of heat generated by the acoustic generator 108 during operation and heat generated in the battery 142 during recharging operations.

The acoustic transducer 144 is captured in the housing 102 by crush ribs 147 and abuts against an annular ledge 149 in the housing 102 adjacent the open end portion 106. Behind the crush ribs 147 is a wall 151 that prevents sound from being transmitted into the end portion 104 of the housing and out through the ventilation openings 150. The wall 151 thus divides the housing 102 and physically separates the acoustic transducer 144 from the acoustic generator 108 in the housing 102.

Figure 7:
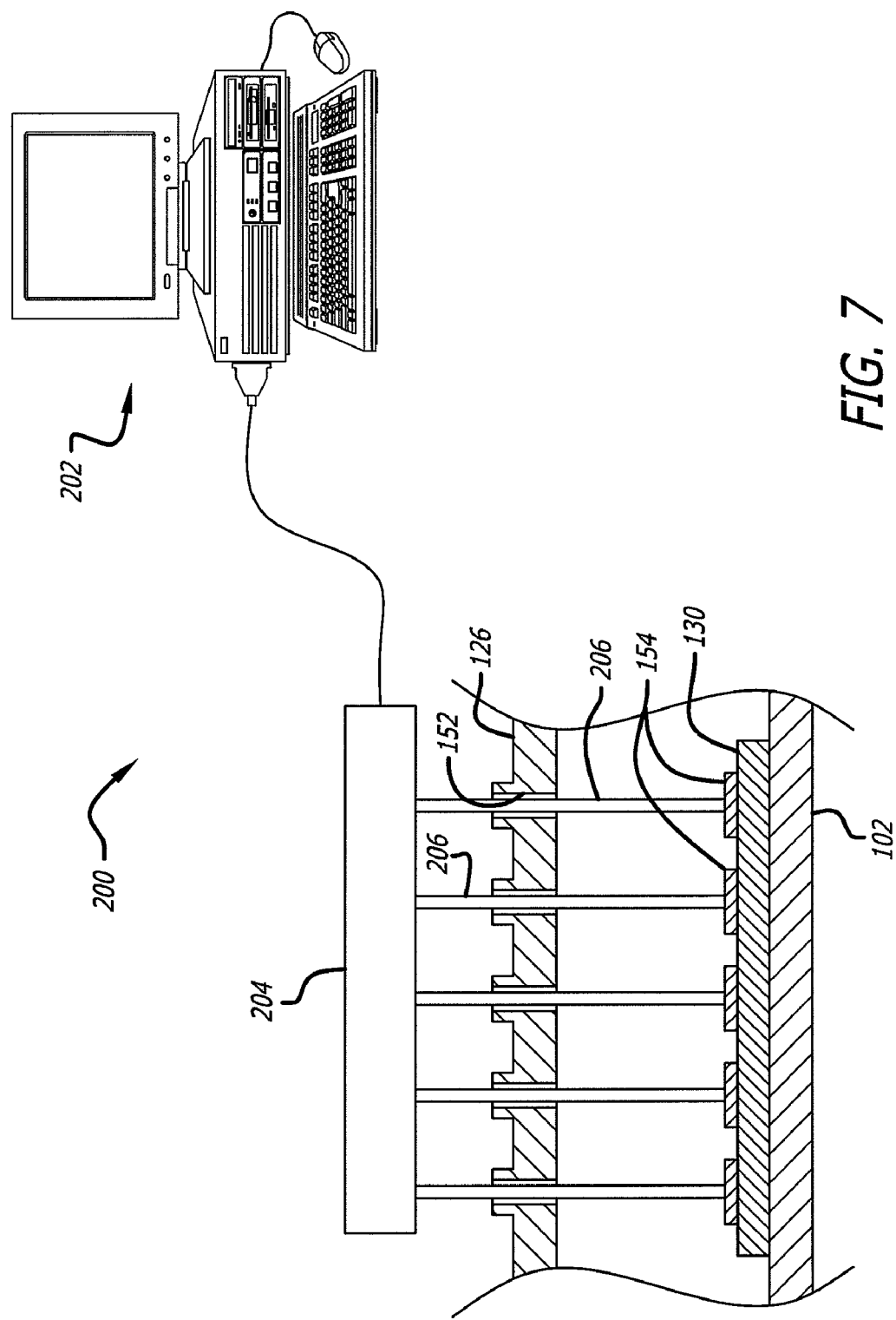
FIG. 7 is a schematic representation of a system for programming the apparatus shown in FIG. 1 without disassembly of the apparatus.

In the embodiment 100 shown in FIGS. 1-8, the right side of the web portion 126 of the housing 102 has a unique series of aligned pin holes 152 therethrough. These pin holes 152 are positioned directly adjacent an underlying set of contact pads 154 on the circuit board 130. Referring now to FIG. 7, a system 200 for programming the apparatus 100 is schematically shown. The system 200 includes a personal computer 202, a probe connector 204 connected to a port on the computer 202. The connector 204 has a series of spaced parallel connection pins 206. The probe connector 204 is positioned such that the pins 206 pass through the holes 152 in the web portion 126 of the housing 102 to contact the pads 154. The personal computer 202 can then be used to provide instructions to the microprocessor 128 to provide, for example, control parameters for a predefined series of acoustic waveforms to be generated by the transducer in an automated mode of operation of the acoustic generator 108.

This configuration of the housing 102 with the series of aligned holes in the web portion 126 uniquely permits external management and programming of the acoustic generator 108 without having to disassemble the apparatus 100. Thus a respiratory therapist or physician can program the apparatus 100 to deliver a predetermined or customized sequence of acoustic pulses/vibrations to the user that optimally dislodges and loosens phlegm in the patient's lungs and airways.

The apparatus 100 may alternatively be equipped with a Bluetooth, infrared, or other wireless transceiver or receiver coupled with or integrated onto the circuit board 130 that is coupled to the microprocessor 128 so that the acoustic generator 108 can be remotely programmed without the necessity for physical interconnection with the computer 202 through the pin holes 152. Such a wireless connection with the microprocessor 128 can facilitate automatic control of the pulse rate, volume, frequency and/or mode of operation of the apparatus 100 in response to feed-forward or feedback from an external wireless transducer 129 before, during or after operation of apparatus 100. The wireless transducer 129 may be an electronic stethoscope, blood oxy-meter, or other such device monitoring performance of the patient's breathing during operation of the apparatus 100.

To protect the acoustic generator 108 components from contamination by fluid and particulate matter transmitted by the patient into the coupling chamber 110, a disposable diaphragm 160 is sandwiched between the mouthpiece 112 and the housing 102. This diaphragm 160 spans the coupling chamber 110, provides a barrier to such matter, and permits free transmission therethrough of the acoustic vibrations produced by the acoustic transducer 144. The diaphragm 160 has a pliable, deformable resilient annular rim 162 and an acoustically transmissive resilient plastic sheet 164 stretched over, across and fastened to the rim 162. This sheet 164 is preferably a thin polyethylene film that is heat staked to the rim 162. The rim 162 of the diaphragm 160 preferably has a peripheral annular groove 166 that fits over a complementary annular ridge 168 formed in the large end 114 of the mouthpiece 112. The open end portion 106 of the housing 102 has an annular flat flange 170. This flat flange 170 presses against the rim 162 of the diaphragm 160 when the housing 102 is joined to the mouthpiece 112 with the diaphragm 160 sandwiched therebetween as is shown in the partial sectional view of FIG. 6. In alternative embodiments of the apparatus 100, the disposable diaphragm 160 may be incorporated permanently into the mouthpiece 112. In such an alternative, the entire mouthpiece 112 would preferably be disposable.

The preferably threaded joint between the housing 102 and the mouthpiece 112 contains two acoustic barriers to external transmission of the acoustic vibrations produced by the generator 108. A first barrier is formed by the diaphragm rim 162 that is sandwiched between the flange 170 and the ridge 168. This first barrier dampens sounds from passing between the threaded end 114 and the threads 190 on the open end 116. Second, the open end 106 has an annular lip 192 spaced from the threads 190 that fits into a corresponding annular recess 194 around the open end 114 of the mouthpiece 112 that prevents dampened sound from escaping the joint. The provision of these two separate barriers permits the apparatus 100 to be used by a patient in close proximity to bystanders without disrupting such activities as watching television or conducting relatively normal voice conversations.

Figure 4:
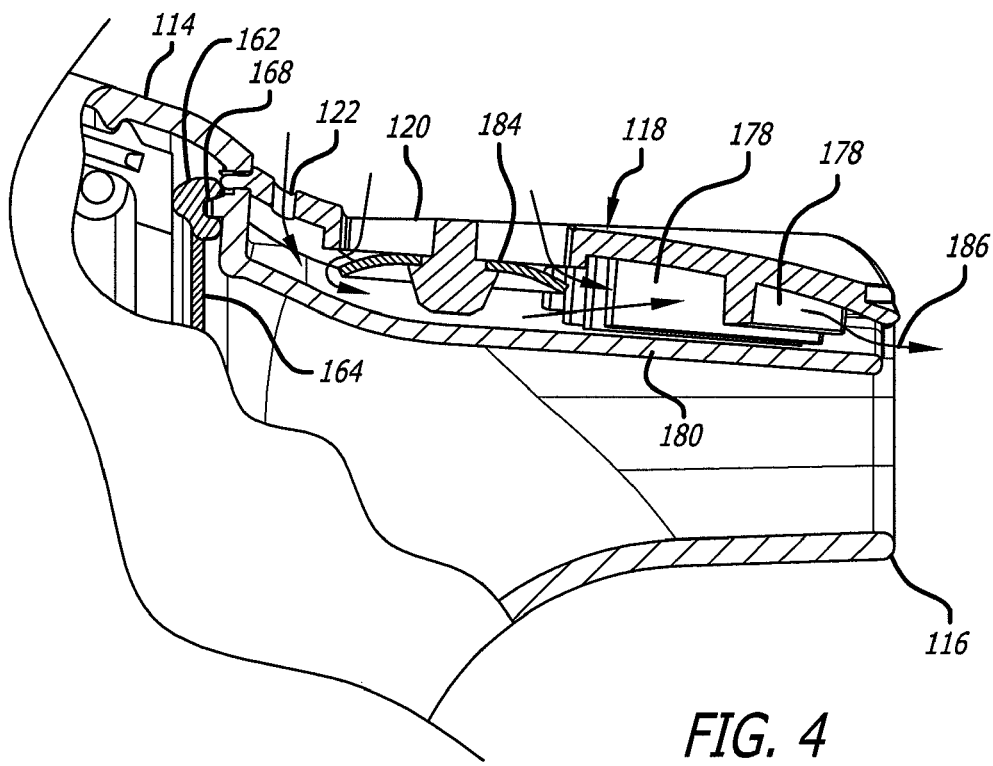
FIG. 4 is a partial right side view as in FIG. 1 of the mouthpiece portion of the apparatus showing air flow during inhalation.
Figure 5:
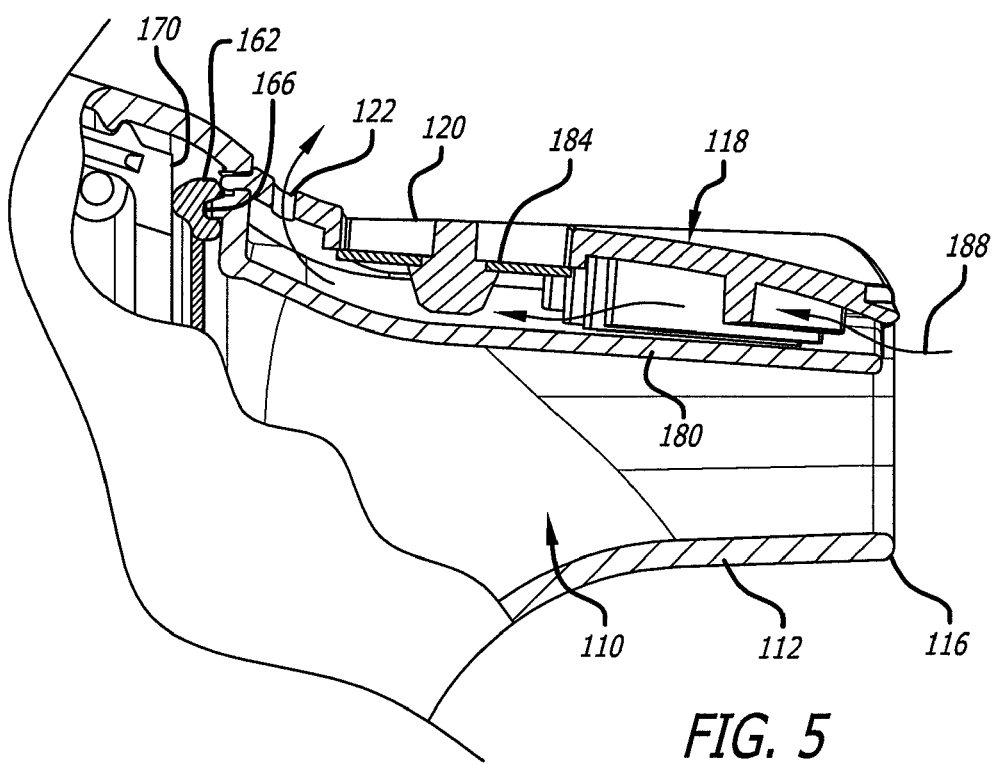
FIG. 5 is a partial right side view as in FIG. 4 showing air flow during exhalation.

Valve 118 is preferably a separate, removable insert member 176 slidably disposed in a recess 180 formed in the mouthpiece 112. The valve member 176 is preferably an injection molded body having a series of passages 178 leading from the open end 116 of the mouthpiece 112 to an underside of the valve opening 120 and to the bypass openings 122. The valve opening 120 is closed by a flexible rubber or plastic valve disc 184. As is best shown in FIG. 4, as a patient inhales through the apparatus 100, fresh air is brought through the valve 118 through the openings 122 and the valve opening 120 past the valve disc 184, through the passages 178 as shown by the directional flow arrows 186, and out of the mouthpiece 116 into the patient's airways. During exhalation, air flows in the direction shown in FIG. 5. Exhaled hair enters the mouthpiece 116 as shown by arrow 188, flows through the passages 178, and out through the bypass openings 122.

Since the bypass openings 122 present a smaller cross sectional area for exhaust than a combination of the bypass openings 122 plus the valve opening, 120, exhaled air flow is restricted, causing a positive back pressure into the patient's lungs. The presence of a small back pressure against exhalation has been found to enhance breakup and subsequent expulsion of the phlegm and mucus buildup in a patient's lungs and airways. The amount of back pressure is regulated by the size and number of bypass openings 122. In the presently preferred embodiment shown in FIGS. 1-8, three openings 122 are provided in the removable valve 118. The valve 118 is removable for cleaning, and may be replaced with another valve 118 having larger or smaller bypass openings 122 as may be needed by a particular patient.

Another configuration of the body 176, not shown, may include a fitting, such as a socket, for attachment on the valve 118 of a medicinal inhalation device over the valve opening 120. Such a configuration would permit an inhaler to be administered in conjunction with use of the apparatus 100. Alternatively, the valve 118 may be of a configuration to entirely enclose a medicinal inhalation device, as the valve 118 is removable from the mouthpiece 112. Thus the configuration of the valve 118 in the embodiment shown in FIGS. 1 through 8 is merely exemplary.

Although the apparatus 100 is primarily configured for use by human patients, it may be used for a variety of other patients, such as horses, dogs, cats, or other animals with respiratory diseases that cause nasal passage, bronchial and/or lung congestion. For example, the apparatus 100 may be used directly on horses. A horse does not normally breathe through its mouth. A horse breathes through its two nostrils. In the equine application, the mouthpiece 112 may be used without the valve 118. In this case a blank valve insert may be provided on the mouthpiece 112 that does not have breathing passages through it as above described. In this case, the patient, the horse, breathes through one nostril while the apparatus 100 provides acoustic vibrations through the other nostril.

FIGS. 9 through 14 show an exemplary mouthpiece 300 that may be utilized with bovine, equine, and other animal patients for which a valve 118 is not needed. This mouthpiece 300 simply replaces the mouthpiece 112 shown in FIGS. 1-6 and 8. The remainder of the apparatus 100 is as described above. In actuality, the illustrated mouthpiece 300 is actually inserted into a large animal patient's nostril rather than the patient's mouth. The terminology of "mouthpiece", therefore, is used generically herein to designate that portion of the apparatus 100, that, when attached to the housing 102, directs the acoustic energy into a patient's airways.

Figure 9:
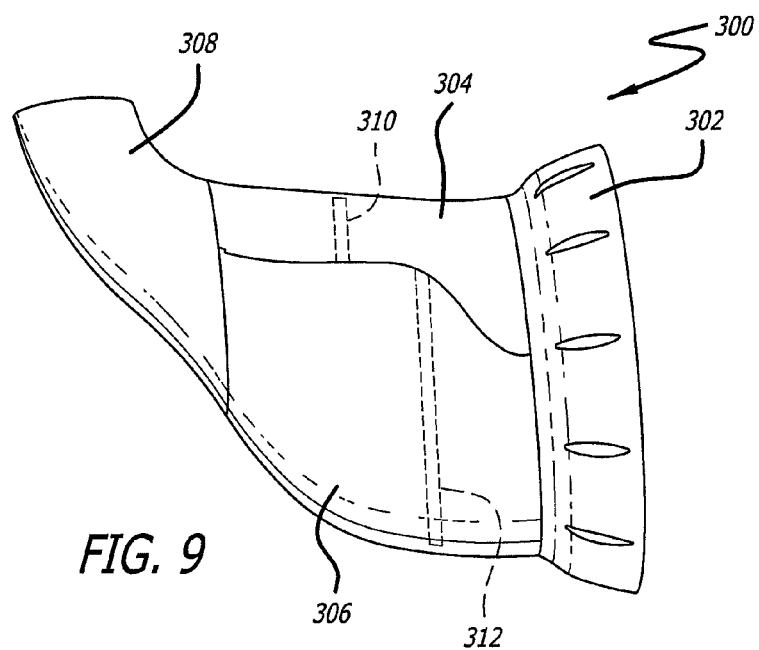
FIG. 9 is an assembled side view of a mouthpiece in accordance with another embodiment for use in certain applications adapted to be attached to the housing shown in FIG. 8.
Figure 10:
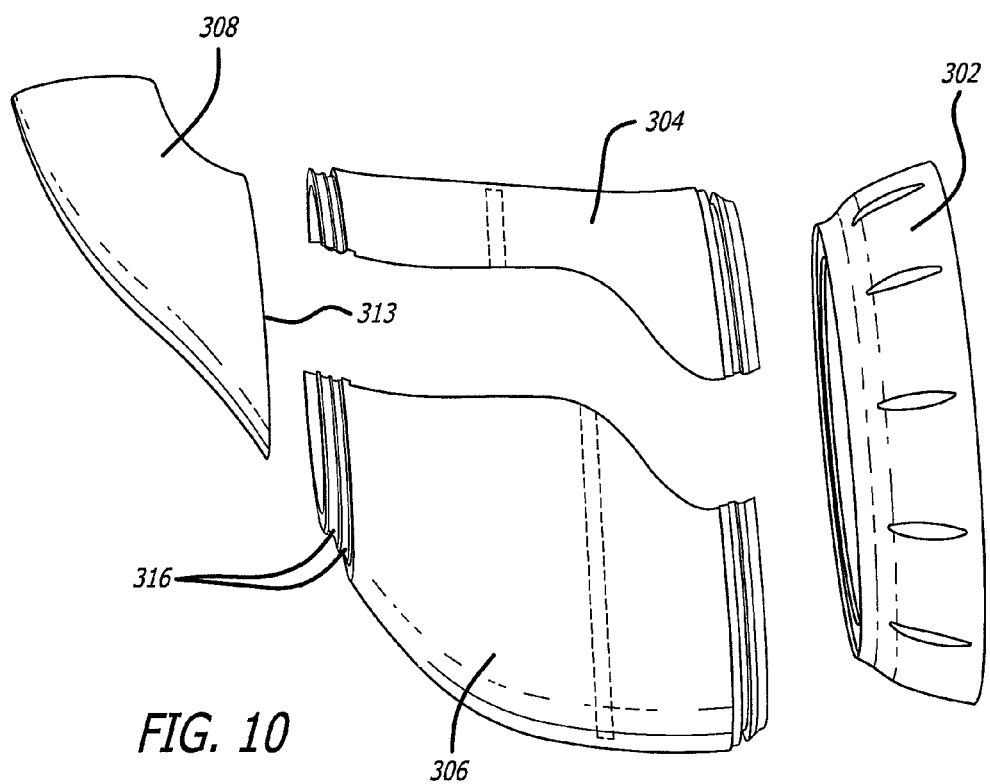
FIG. 10 is an exploded side perspective view of the mouthpiece shown in FIG. 9.
Figure 11:
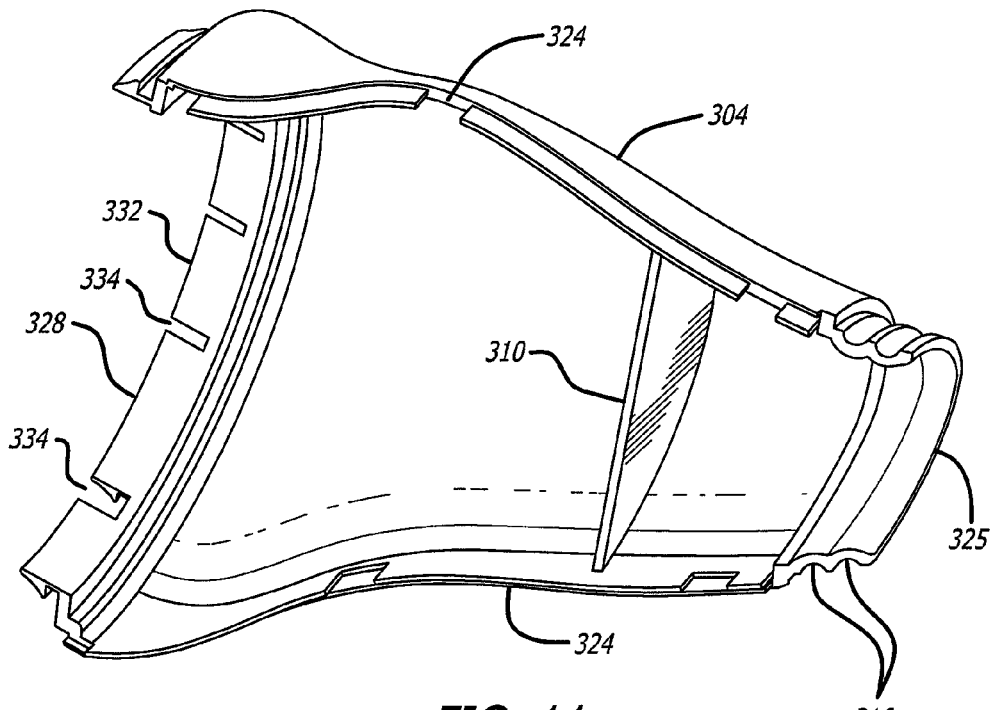
FIG. 11 is a separate perspective inside view of an upper baffle section of the mouthpiece shown in FIG. 9.
Figure 12:
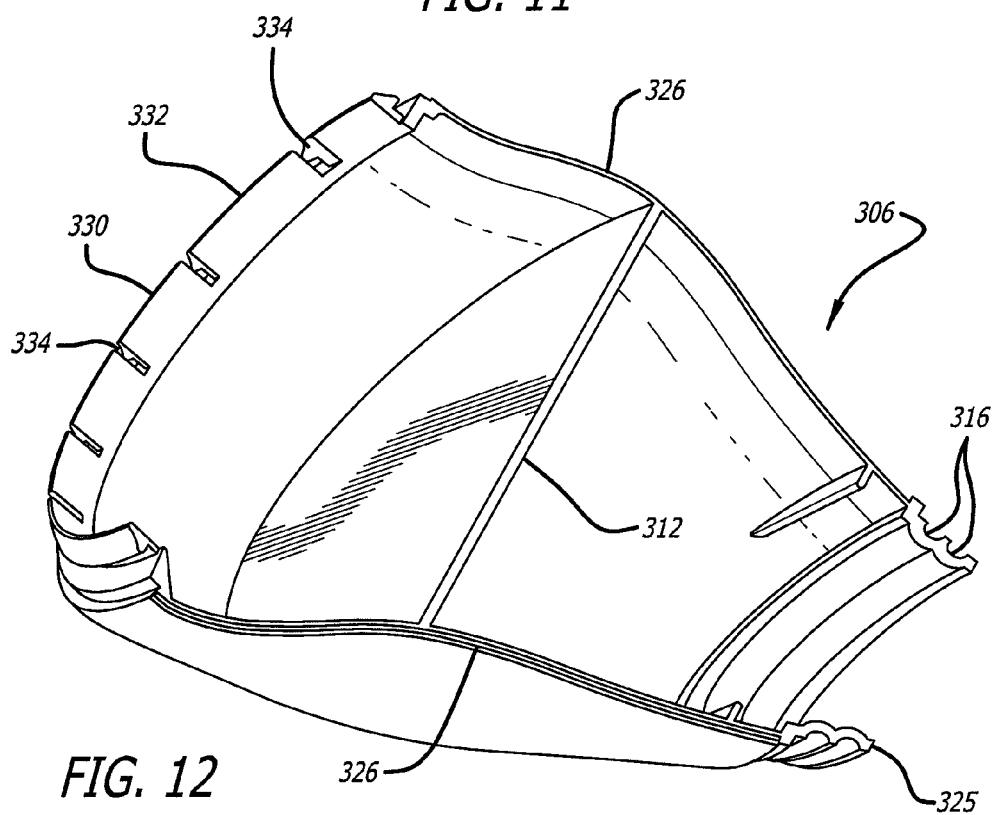
FIG. 12 is a separate perspective inside view of the lower baffle section of the mouthpiece shown in FIG. 9.

The mouthpiece 300 consists of a base ring 302, an upper baffle section 304, a lower baffle section 306, and a flexible tip section 308. The upper baffle section and lower baffle sections snap fit together as is shown in FIG. 9. Together the upper and lower baffle sections 304 and 306 are inserted into and retained by the ring shaped base ring 302 such that the joined sections 304 and 306 may be rotated within the ring shaped base ring 302. The ring shaped base 302, in turn, is threaded onto the open threaded end 106 of the housing 102 as above described with reference to the embodiment 100 shown in FIGS. 1-8.

The upper and lower baffle sections 304 and 306 each include a preferably rigid internal shelf 310 and 312 respectively, axially spaced from each other such that, when the mouthpiece 300 is inserted into an animal's nostril, fluid expelled from the patient's nasal cavities has to follow a tortuous path toward the diaphragm 162 and thus will generally be caught by at least one of the baffles (310 and/or 312) rather than reaching and impinging on the replaceable diaphragm 160. The lower baffle 312 preferably also has a central notch 313 to permit passage of the acoustic energy therethrough so that the baffles do not substantively diminish the acoustic energy transmission, while still providing a mechanism to catch the expelled fluidic materials.

Figure 13:
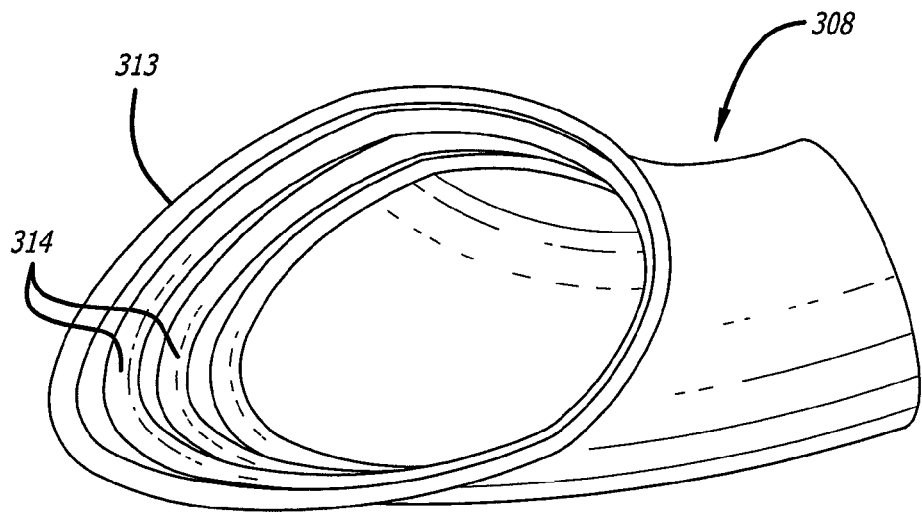
FIG. 13 is a separate perspective view of the nose section of the mouthpiece shown in FIG. 9.

The flexible, tapered, tubular tip section 308 is separately shown in FIG. 13. The tip section 308 is formed of a soft latex or silicon plastic material. The proximal end 313 of the tip section 308 preferably has an annular internal groove 314 that receives tapered annular barb portions 316 formed at the distal end 325 of the mated upper and lower sections 304 and 306 to assemble the mouthpiece 300 as shown in FIG. 9. The tip section 308 is preferably made relatively soft and flexible to interface with the patient's nasal tissues comfortably without danger of irritation or injury. In addition, the rear end of the tip section 308 preferably elastically stretches to permit the barb portions 316 to enter the groove 314 to retain the tip section 308 on the assembled baffle sections 304 and 306.

Figure 14:
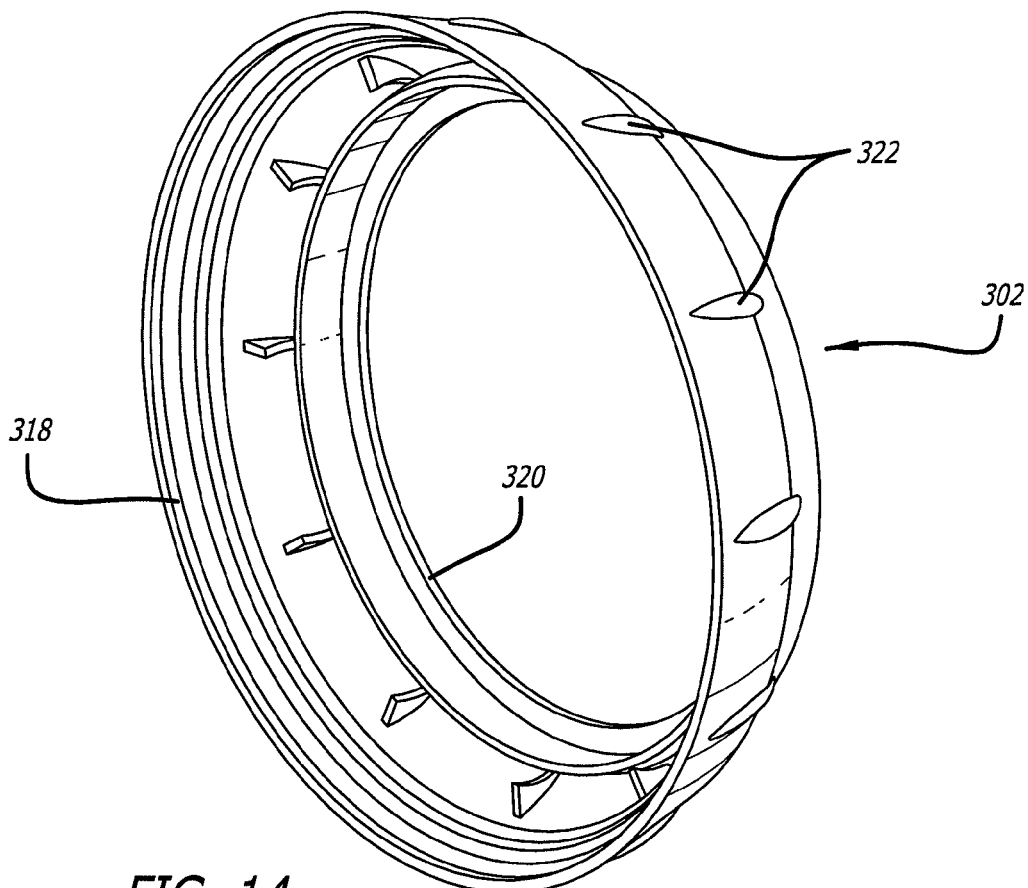
FIG. 14 is a separate perspective view of the attachment ring of the mouthpiece shown in FIG. 9.

The base ring 302 is separately shown in FIG. 14. This base ring 302 is an annular, substantially rigid plastic body having an internally threaded end 318 sized to thread onto the externally threaded end 106 of the housing 102 shown in FIG. 8. The other open end of the base 302 has an internal annular flange 320. The external surface of the base ring 302 has a series of spaced protrusions 322 that facilitate assembly of the base ring 302 onto the housing 102.

Referring back now to FIGS. 11 and 12, the upper and lower sections 304 and 306 mate together along mating tongue and groove edges 324 and 326. The large ends 328 and 330 of these sections 304 and 306 together form an annular, externally tapered, sleeve 332 that has a series of spaced cutouts or notches 334. This tapered sleeve 332 snaps into and engages with the annular flange 320 in the other open end of the base ring 302. The base ring 302 thus retains the upper and lower sections 304 and 306 together and permits the joined upper and lower sections 304 and 306, together with the tip 308, to be rotated about the ring base 302, and thus the housing 102. Thus, referring to FIG. 9, if the mouthpiece 300 were fastened to the housing 102, the tip 308 may be rotated to orient the tip 308 up, down, or at any angle while retaining the base ring 302 stationary on the housing 102.

The upper and lower sections 304 and 306 mate together preferably in a tongue and groove fashion. However, in alternative embodiments, this joint between the mating sections may be a butt joint since the base ring 302 and the tip section 308 actually hold these sections 304 and 306 together. Also, in other alternative embodiments, the baffles 310 and 312 may be eliminated or have a shape other than that shown. The base ring 302 and the upper and lower sections 304 and 306 are preferably made of a substantially rigid plastic material, preferably one that may be autoclaved. The tip section 308 may have a shape other than as specifically shown, depending on the particular animal for which it is designed.

While the apparatus has been described in terms of what are presently considered to be the most practical and preferred embodiments, it is to be understood that the disclosure need not be limited to the disclosed embodiments. For example, other housing shapes than housing 102 are envisioned. For example, the housing 102 need not be a curved "C" shape with the electronics carried in a web portion between portions 104 and 106. Other functions, placements and configurations of the control buttons or control mechanisms may be utilized. In addition, other shapes and configurations of the housing 102 are envisioned.

Further, the control mechanisms and buttons may be replaced by automated functionality in alternative embodiments. It is intended that this disclosure cover various modifications and similar arrangements included within the spirit and scope of the claims, the scope of which should be accorded the broadest interpretation so as to encompass all such modifications and similar structures. All patents and other printed publications referred to herein are hereby incorporated by reference in their entirety. The present disclosure includes any and all embodiments of the following claims.

The invention claimed is:

1. An apparatus for assisting a patient in loosening and/or clearing fluids, phlegm and mucus collected in a patient's sinuses, lungs, bronchial and/or tracheal passages comprising:
   an elongated curved hollow housing having a substantially closed end portion and an open end portion, the open end portion forming at least part of an acoustic coupling chamber;
   a substantially funnel shaped mouthpiece having a large end adapted to fit onto the open end portion of the housing and a small end portion sized to be inserted into a patient's airways, the mouthpiece forming another part of the acoustic coupling chamber;
   an acoustic signal generator housed within said hollow housing having an acoustic transducer directing acoustic vibrations into and through the coupling chamber into a patient's airways when the mouthpiece is coupled into the patient's airways; and
   a flexible disposable diaphragm in the coupling chamber sandwiched between the mouthpiece and the hollow housing, the diaphragm having a resilient plastic annular rim within the housing engaging an annular flange around the open end of the housing when the mouthpiece and housing are joined, the rim forming a first acoustic seal between the coupling chamber and an external environment, wherein the open end portion of the housing has a peripheral annular flange adjacent the open end and wherein a portion of the mouthpiece engages the annular flange to form a second acoustic seal between the coupling chamber and the external environment wherein the mouthpiece has an internal annular ridge spaced from the open end and the disposable diaphragm rim has a complementary shaped groove receiving the ridge.

2. The apparatus according to claim 1 wherein the acoustic signal generator includes a control circuit board and microprocessor connected to the transducer for selectively controlling the frequency and repetition rate of the acoustic vibrations produced by the transducer, and the housing further comprises a web portion between the closed end portion and the open end portion, the web portion supporting the control circuit board and microprocessor therein.

3. The apparatus according to claim 2 further comprising a slide switch movably extending through a portion of the curved housing for controlling one or more acoustic parameters associated with the acoustic vibrations.

4. The apparatus according to claim 2 wherein the web portion has a plurality of resilient control switch pads coupled to the signal generator for adjusting control parameters for the acoustic vibrations produced by the acoustic transducer in the coupling chamber.

5. An apparatus for assisting a patient in loosening and/or clearing fluids, phlegm and mucus collected in a patient's sinuses, lungs, bronchial and/or tracheal passages comprising:
   an elongated curved hollow housing having a substantially closed end portion and an open end portion, the open end portion forming at least part of an acoustic coupling chamber;
   a substantially funnel shaped mouthpiece having a large end adapted to fit onto the open end portion of the housing, and to a small end portion sized to be inserted into a patient's airways, the mouthpiece forming another part of the acoustic coupling chamber, wherein the mouthpiece includes a valve operable to permit a patient breathing through the mouthpiece to inhale through a valve opening and exhale through a bypass passage around the valve while coupling the acoustic coupling chamber into the patient's mouth, wherein the valve comprises a separate removable insert member slidably disposed in a recess formed in the mouthpiece, the insert member having one or more passages leading from the open small end of the mouthpiece to a valve opening and to one or more bypass openings, and a flexible valve disc disposed in the valve opening operable to permit passage of a gas through the valve opening in a first direction and block passage of the gas through the valve opening in a second direction;
   a flexible disposable diaphragm in the coupling chamber sandwiched between the mouthpiece and the hollow housing, the diaphragm having a resilient plastic annular rim within the housing engaging an annular flange around the open end of the housing when the mouthpiece and housing are joined, the rim forming a first acoustic seal between the coupling chamber and an external environment, wherein the open end portion of the housing has a peripheral annular flange adjacent the open end and wherein a portion of the mouthpiece engages the annular flange to form a second acoustic seal between the coupling chamber and the external environment, wherein the mouthpiece has an internal annular ridge spaced from the open end and the disposable diaphragm rim has a complementary shaped groove receiving the ridge; and
   an acoustic signal generator housed within said hollow housing having an acoustic transducer directing acoustic vibrations into and through the coupling chamber into a patient's airways when the mouthpiece is coupled into the patient's airways.

6. The apparatus according to claim 5 wherein the acoustic signal generator includes a control circuit board and microprocessor connected to the transducer for selectively controlling the frequency and repetition rate of the acoustic vibrations produced by the transducer, and the housing further comprises a web portion between the closed end portion and the open end portion, the web portion supporting the control circuit board and microprocessor therein.

7. The apparatus according to claim 5 further comprising a slide switch movably extending through a portion of the curved housing for controlling one or more acoustic parameters associated with the acoustic vibrations.

8. The apparatus according to claim 6 wherein the web portion has a plurality of resilient control switch pads coupled to the signal generator for adjusting control parameters for the acoustic vibrations produced by the acoustic transducer in the coupling chamber.

* * * * *